(12) United States Patent
Meyer et al.

(10) Patent No.: US 8,094,907 B1
(45) Date of Patent: Jan. 10, 2012

(54) SYSTEM, METHOD AND COMPUTER PROGRAM PRODUCT FOR FAST CONJUGATE PHASE RECONSTRUCTION BASED ON POLYNOMIAL APPROXIMATION

(75) Inventors: Craig H. Meyer, Charlottesville, VA (US); Weitian Chen, Union City, CA (US); Christopher T. Sica, Charlottesville, VA (US)

(73) Assignee: University of Virginia, Charlottesville, VA (US)

( * ) Notice: Subject to any disclaimer, the term of this patent is extended or adjusted under 35 U.S.C. 154(b) by 922 days.

(21) Appl. No.: 12/114,307

(22) Filed: May 2, 2008

Related U.S. Application Data

(60) Provisional application No. 60/927,462, filed on May 3, 2007, provisional application No. 60/930,882, filed on May 18, 2007, provisional application No. 60/989,178, filed on Nov. 20, 2007.

(51) Int. Cl.
*A61B 6/03* (2006.01)
(52) U.S. Cl. ........................................... 382/131
(58) Field of Classification Search .......... 382/128–132; 324/300–322
See application file for complete search history.

(56) References Cited

U.S. PATENT DOCUMENTS 7,545,966 B2 * 6/2009 Lewin et al. .................. 382/128

OTHER PUBLICATIONS

Chen et al., Fast conjugate reconstruction using Taylor series approximation, May 19, 2007, Proceedings of the International Society of Magnetic Imaging in Medicine, vol. 15, p. 148.*
Chen et al., Fast Automatic Linear Off-Resonance Correction Method for Spiral Imaging, Jun. 29, 2006, Magnetic Resonance in Medicine, vol. 56, pp. 457-462.*
Noll et al., Conjugate Phase MRI Reconstruction with Spatially Variant Sample Density Correction, Mar. 2006, IEEE Transactions on Medical Imaging, vol. 24, No. 3, pp. 325-336.*
King et al, Concomitant gradient field effects in spiral scans. *Magn Reson Med* 1999; 41: 103-112.

* cited by examiner

*Primary Examiner* — Edward Glick
*Assistant Examiner* — John Corbett
(74) *Attorney, Agent, or Firm* — Blank Rome LLP

(57) ABSTRACT

A fast conjugate phase reconstruction method for MRI is based on a polynomial expansion of the off-resonance phase accrual term. The expansion is truncated and can be a Taylor or Chebyshev expansion.

28 Claims, 10 Drawing Sheets

Figure 8A
Figure 8B
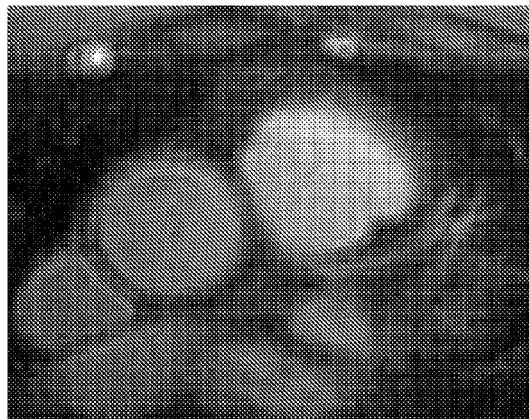
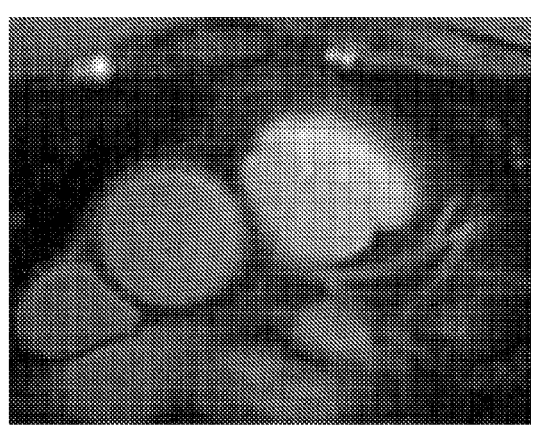
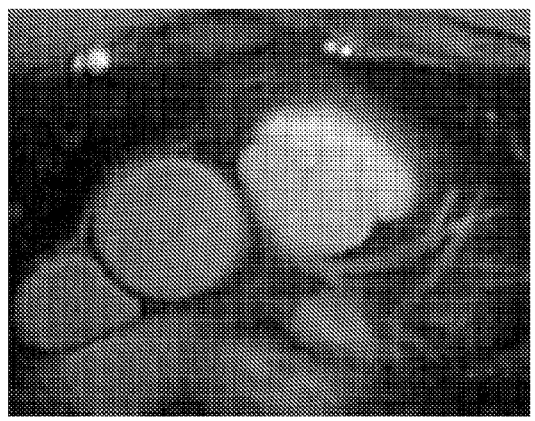
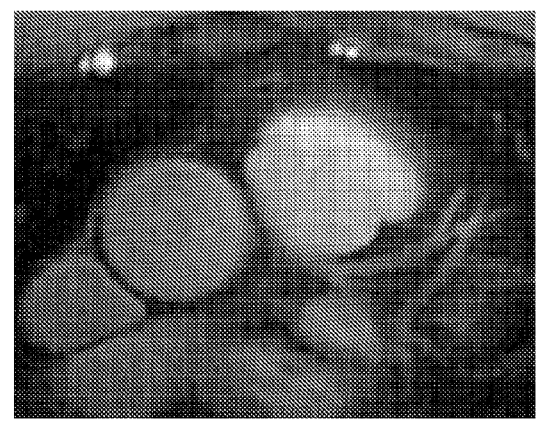
Figure 8C
Figure 8D

SYSTEM, METHOD AND COMPUTER PROGRAM PRODUCT FOR FAST CONJUGATE PHASE RECONSTRUCTION BASED ON POLYNOMIAL APPROXIMATION

REFERENCE TO RELATED APPLICATION

The present application claims the benefit of U.S. Provisional Application Nos. 60/927,462, filed May 3, 2007; 60/930,882, filed May 18, 2007; and 60/989,178, filed Nov. 20, 2007, whose disclosures are hereby incorporated by reference in their entireties into the present application.

STATEMENT OF GOVERNMENT INTEREST

The work leading up to the present invention was supported by NIH Grant No. HL079110. The government has certain rights in the invention.

FIELD OF THE INVENTION

The present invention is directed to phase reconstruction in imaging and more particularly to conjugate phase reconstruction based on a polynomial (e.g., Taylor or Chebyshev) approximation of the off-resonance phase accrual term.

DESCRIPTION OF RELATED ART

Off-resonance effects are common in magnetic resonance imaging (MRI). In contrast to Cartesian acquisitions, where off-resonance effects usually cause only geometrical distortion and intensity variations, off-resonance effects can cause unacceptable image degradation in non-Cartesian acquisitions. In particular, uncorrected off-resonance causes space-variant image blurring in spiral k-space scanning This issue has been long recognized and is one of the most challenging problems in non-Cartesian MRI.

Off-resonance effects in MRI can arise from various sources. The off-resonance from chemical shift usually can be addressed by presaturation RF pulses or spectral-spatial excitation. Another source of off-resonance effects is B0 field inhomogeneity, including susceptibility-induced field inhomogeneity and main field inhomogeneity. Off-resonance effects can also come from concomitant gradient fields. The combination of a static main field and linear gradients as applied in MRI do not satisfy Maxwell's equations of electrodynamics. As a result, additional magnetic field terms known as concomitant gradients arise. When the off-resonance phase from B0 field inhomogeneity and concomitant gradients are both present, correction of only one of them is insufficient and sometimes can even increase blurring artifacts in some parts of the image.

Field inhomogeneity commonly exists in MRI and becomes more significant at high field strength. Field inhomogeneity causes geometrical distortion and intensity variations for acquisition using Cartesian trajectories. For acquisition using non-Cartesian trajectories, such as spiral or radial trajectories, field inhomogeneity causes image blurring artifacts, which can impair the diagnostic value of the images.

Since both B0 field inhomogeneity and concomitant gradient fields vary slowly in space, we would expect that conjugate phase (CP) reconstruction can afford effective simultaneous correction of both off-resonance effects. However, direct calculation of CP reconstruction is very time consuming. Fast alternatives to CP reconstruction with comparable accuracy have been developed, including time approximation methods, frequency approximation methods, and polynomial approximation methods. Each of these methods was originally developed for B0 field inhomogeneity correction. King et al (King K F, Ganin A, Zhou X J, Bernstein M A. Concomitant gradient field effects in spiral scans. *Magn Reson Med* 1999; 41: 103-112) discussed how to extend fast CP methods for concomitant field correction in spiral imaging. No literature to date has discussed in detail simultaneous B0 inhomogeneity and concomitant field correction in non-Cartesian MRI.

Conjugate phase reconstruction and its fast approximations are widely used methods of compensating for field inhomogeneity effects. Ignoring T2 relaxation, conjugate phase reconstruction can be expressed as:

$$m_{CP}(r) = \int s(t) W(t) \exp(j(2\pi k(t) \cdot r + \Delta\omega(r)t)) dt \quad [1]$$

where $s(t)$, $k(t)$, $\Delta\omega(r)$, and $w(t)$ are the time signal, k-space trajectory, field inhomogeneity, and the density compensation accounting for the non-uniformity of the data sampling in k-space, respectively. Direct computation of Eq. [1] is time consuming. Fast approximations include time-segmented reconstruction, frequency-segmented reconstruction, and mutlifrequency interpolation. All of these methods reduce the computation cost of conjugate phase reconstruction by employing different approximations for the off-resonance phase accrual term $\exp(j\Delta\omega(r)t)$. However, a technique offering both accuracy and computational efficiency is still needed.

SUMMARY OF THE INVENTION

It is therefore an object of the invention to provide such a technique.

To achieve the above and other objects, the present invention is directed to conjugate phase reconstruction based on a polynomial approximation (e.g., Taylor or Chebyshev) of the off-resonance phase accrual term.

In at least some embodiments, the present invention implements a new fast conjugate phase reconstruction method based on a polynomial expansion of the off-resonance phase accrual term. This algorithm achieves high approximation accuracy and can be performed rapidly with the developed computational strategies. The aspects of the present invention method and algorithm may be implemented as a computer method, system, computer system, and computer program product. Further, the aforementioned present invention method, system, computer method, computer system and computer program product may be implemented with MRI systems, MRI subsystems and various types of computer processors and computer related systems and components.

In one of the preferred embodiments, we introduce a new fast alternative to CP reconstruction, where the off-resonance phase term is approximated by its Chebyshev polynomials. Compared to similar ideas discussed in the past, that embodiment is more computationally efficient and is well-suited for simultaneous B0 inhomogeneity and concomitant field correction. We apply the technique to deblurring images acquired using spiral scanning. We also demonstrate that the proposed method is efficient for combined semi-automatic inhomogeneity correction and concomitant field correction. Semi-automatic correction is accurate even with an inaccurate or low-resolution field map.

B0 field inhomogeneity and concomitant gradient fields can cause image degradation in non-Cartesian MRI. We propose an efficient algorithm for simultaneous B0 inhomogeneity and concomitant field correction in non-Cartesian MRI. Our algorithm is a fast alternative to CP reconstruction with the off-resonance phase term approximated by Chebyshev polynomials. Conventional B0 map acquisition can be inaccurate in some applications. We demonstrated that the proposed algorithms can be employed for combined semi-automatic correction and concomitant field correction to address this problem.

The algorithms are computationally efficient. The interpolation coefficients are object-independent and can be precalculated and used for any sequence with a given trajectory. Since the number of base images required is proportional to the off-resonance frequency range, linear concomitant field correction is incorporated to reduce the computational cost. Incorporation of linear B0 inhomogeneity correction is also desirable in many applications to reduce computational cost when the B0 inhomogeneity is not highly non-linear. To reduce the number of gridding operations, we also interchange the sequence of gridding operation and multiplication of modified sampling time when calculating base images.

During our experiments, we found that automatic off-resonance correction and semi-automatic off-resonance correction can sometimes achieve comparable results to combined B0 inhomogeneity and concomitant field correction when the concomitant gradient field is mild or moderate. The rationale behind this is that, in automatic or semi-automatic correction, the off-resonance phase $\phi(\Delta\omega(r),\Delta\omega_c(r),t)$ is approximated as a spatially-dependent angular off-resonance frequency times t, which is equivalent to approximating $t_c$ as $\alpha t$, where $\alpha$ is a constant. This approximation is reasonable for the spiral gradients designed in our sequences, because the latter part of the spiral gradients has constant magnitude. Consequently, automatic correction and semi-automatic correction can achieve modest simultaneous B0 inhomogeneity correction and concomitant field correction even without explicitly including a concomitant field term. We constrained the searching range of off-resonance frequency within ±50 Hz from the acquired B0 map when performing semi-automatic correction on acquired data sets. A least square fit of $\alpha t$ to $t_c$ from our spiral gradient indicates that ±50 Hz B0 off-resonance frequency corresponds to about ±100 Hz searching range of concomitant field off-resonance frequency. This is sufficient for a moderate concomitant field, especially after incorporating linear concomitant field correction. A larger searching range can be employed in semi-automatic correction to accommodate a stronger concomitant gradient field. Automatic off-resonance correction does not have this issue since the searching range is not constrained by the B0 field map.

We focused on fast CP reconstruction in the preferred embodiments. The idea of approximating a phase term by a Chebyshev or other polynomial can be applied to other image reconstruction methods where off-resonance phase is a concern, such as SPHERE and off-resonance correction based on iterative reconstruction.

We only discussed the concomitant gradient field arising from spiral gradients in this paper. Since arbitrary time-varying phase terms can be approximated by Chebyshev or other polynomials, the present invention should be able to address the concomitant gradient field from a more general readout gradient. The present invention is also likely capable of addressing other time varying phase terms such as those induced by eddy current effects.

BRIEF DESCRIPTION OF THE DRAWINGS

Preferred embodiments of the present invention will be set forth in detail with reference to the drawings, in which:

FIGS. 8A-8D are images of a joint taken with no correction, linear correction, conjugate phase correction, and the second preferred embodiment, respectively.

DETAILED DESCRIPTION OF THE PREFERRED EMBODIMENTS

Figure 1:
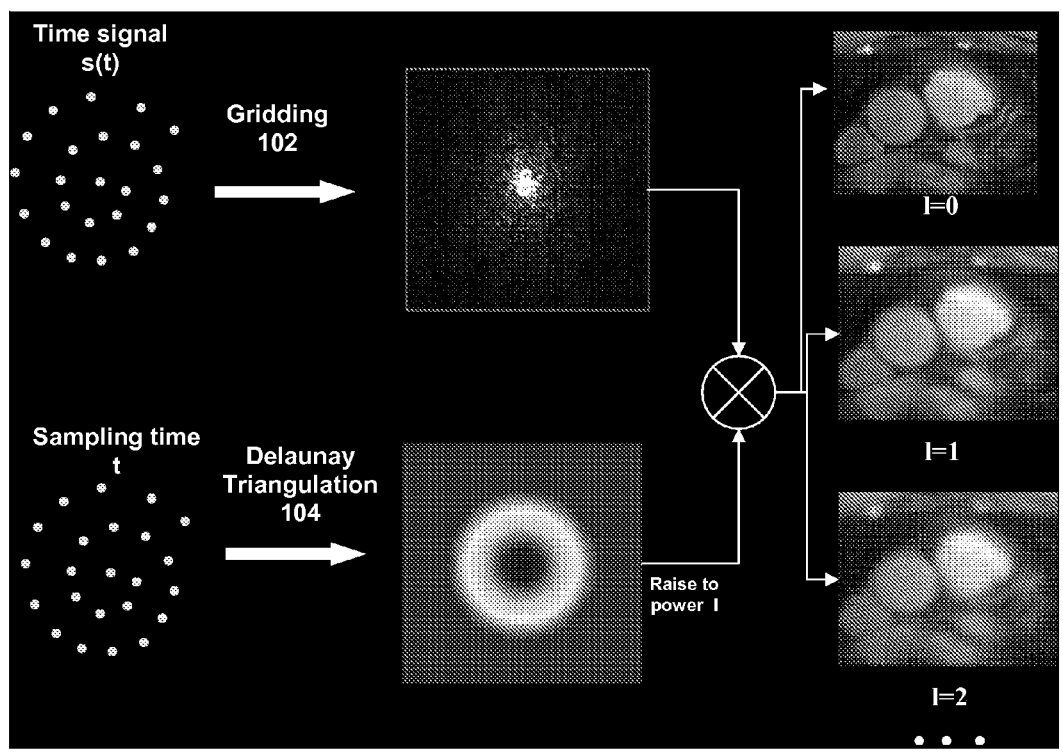
FIG. 1 shows the formation of the base images.

Preferred embodiments of the invention will be set forth in detail with reference to the drawings, in which like reference numerals refer to like elements or steps throughout.

The preferred embodiments use polynomial expansions of the off-resonance phase accrual term, namely, $$e^{j\Delta\omega(r)t} \approx \alpha_0 + \alpha_1 t + \alpha_2 t^2 + \ldots + \alpha_n t^n + \quad [2]$$

The expansions are converging infinite series; however, the approximations terminate the series at some point, as disclosed below.

The first preferred embodiment replaces the phase term with its Taylor expansion, which can be expressed as follows:

$$m_{CP}(r) = \sum_n \frac{[j\Delta\omega(r)]^n}{n!} m_n(r), \quad [3]$$

$$\text{with } m_n(r) = \int_t W(t) t^n \exp[j2\pi k(t) \cdot r] \, dt, \, n = 0, 1$$

, with $m_n(r) = \int_t W(t)s(t)t^n \exp[j2\pi k(t)\cdot r]dt$, $n=0,1$ [3]

where $m_n(r)$ are referred to as base images. The base images can be reconstructed by replacing the time signal s(t) with its multiplication by $t^n$ followed by conventional gridding reconstruction. The direct calculation of the base images requires performing gridding individually for each of them, which is computationally inefficient. In our implementation, as shown in FIG. 1, we perform gridding 102 on the time signal s(t) to acquire a Cartesian time signal, and also interpolate the time t onto a Cartesian grid using Delaunay triangulation 104 to form a Cartesian time mask. To compute the base images, we then simply multiply the Cartesian time signal by the time mask n times and then perform a Fourier transform. Since the time mask is only a function of the k-space trajectory and sampling period, it can be computed off-line if the k-space trajectory and sampling period do not change during the scan.

The number of base images required is proportional to the off-resonance phase accrual, $\Delta\omega(r)t$, which can be reduced by incorporating center frequency or linear off-resonance correction into the algorithm, since the bulk center/linear terms are subtracted from $\Delta\omega(r)$ in the phase term. Equation [3] now can be written as:

$$m_{CP}(r) = \sum_n \frac{[j\Delta\tilde{\omega}(r)]^n}{n!} \tilde{m}_n(r), \quad [4]$$

$$\text{with } \tilde{m}_n(r) = \int_t W'(t)s'(t)t^n \exp[j2\pi k'(t) \cdot r] \, dt, n = 0, 1$$

, with $\ddot{m}_n(r) = \int_t W'(t)s'(t)t^n \exp[j2\pi k'(t) \cdot r]dt$, $n=0,1$ [4]

where $\Delta\ddot{\omega}(r)$ is the residual off-resonance after subtracting the center/linear off-resonance frequency from $\Delta\omega(r)$, $s'(t)$ is the signal demodulated by the center off-resonance frequency, and $W'(t)$ and $k'(t)$ are the updated density compensation function and the warped k-space trajectory, respectively, with the linear off-resonance correction incorporated.

Figure 2A:
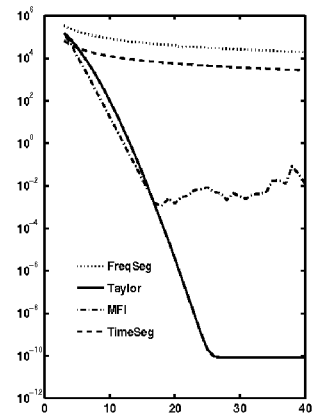
FIGS. 2A and 2B are plots of the approximation error as a function of the number of base images/segments used for the first preferred embodiment.
Figure 2B:
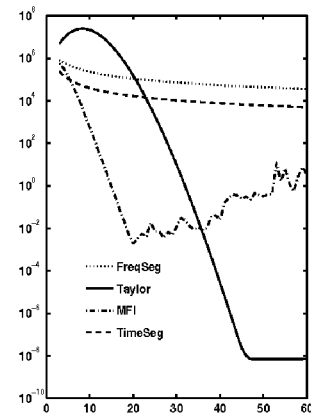

We compared the accuracy of different fast conjugate phase reconstruction methods by simulation studies. The simulation was conducted at two different off-resonance frequency ranges, ±60 Hz and ±100 Hz. The sampling duration was 16.4 ms in each case. At individual off-resonance frequencies with 2 Hz increment within the off-resonance frequency range and at each sampling time point with sampling period 2 microseconds, we calculated the difference between the exact phase term $\exp(j\Delta\omega(r)t)$ and the approximated value from the fast conjugate phase reconstruction methods. The logarithm of the sum of the absolute value of these differences was plotted against the number of base images/segments employed in the fast conjugate phase reconstructions in FIGS. 2A and 2B. More specifically, FIGS. 2A and 2B show semi-log plots of the approximation error (vertical axis) as a function of the number of base images/segments used (horizontal axis). The off-resonance range is ±60 Hz (FIG. 1A) and ±100 Hz (FIG. 1B). The sampling time duration is 16.4 ms.

The simulation studies indicated that the first preferred embodiment (solid lines in FIGS. 2A and 2B) usually requires more base images than the other fast conjugate phase reconstruction methods when the off-resonance phase accrual is relatively large. This problem is mitigated at small off-resonance phase accrual. An advantage of the first preferred embodiment indicated by the simulation is that it can ultimately achieve better approximation accuracy than all the other existing methods.

Figure 3A:
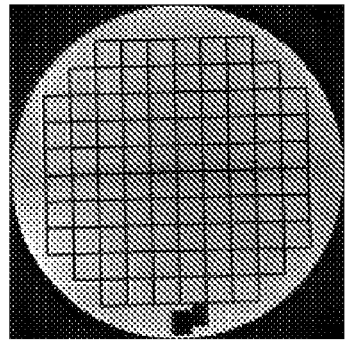
FIG. 3A is an image acquired without deblurring.
Figure 3B:
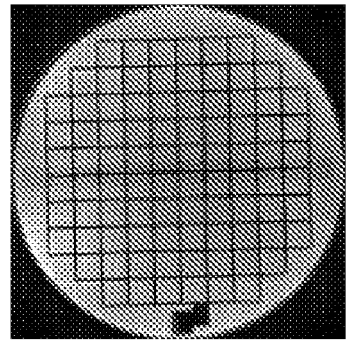
FIG. 3B is an image deblurred in accordance with the first preferred embodiment.

FIGS. 3A and 3B show an off-resonance correction example on a phantom data set acquired using a spiral sequence on a 1.5 T Siemens Avanto scanner. FIG. 3A shows an image acquired without deblurring, while FIG. 3B shows an image deblurred using the first preferred embodiment. The spiral readout was 16.4 ms with 14 interleaves. A low resolution field map was acquired using two single-shot spirals to support off-resonance correction. The deviation of the off-resonance frequency from the bulk frequency is within ±30 Hz and 5 base images were used accordingly. Note that the image blurring was removed after applying the first preferred embodiment. We also performed multifrequency interpolation on the same data set. The off-resonance correction results using the two methods were not visibly different.

The first preferred embodiment usually needs more base images than the other fast conjugate phase reconstruction methods when the off-resonance phase accrual is large. This problem is mitigated by incorporating center frequency or linear off-resonance correction to reduce the off-resonance phase accrual. The Taylor expansion can be performed around non-zero time points. Performing Taylor expansion around a non-zero time point likely can further reduce the number of base images required. T2/T2* decay was ignored in this study. The first preferred embodiment can also be applied to simultaneously compensate T2/T2* decay and off-resonance effect.

A second preferred embodiment uses a Chebyshev expansion rather than a Taylor expansion. As is well known, a function can be expanded into a Chebyshev expansion in the following manner:

$$f(x) = \sum_{k=0}^{\infty} c_k T_k(x) \quad [5]$$

where $T_k(x)$ are the Chebyshev polynomials, defined as $$T_0 = 1, T_1(t) = \left(\frac{2t}{T} - 1\right) \quad [6]$$

$$\ldots$$

$$T_{n+1}(t) = 2\left(\frac{2t}{T} - 1\right)T_n(t) - T_{n-1}(t), n \geq 1$$

In the second preferred embodiment, the off-resonance phase accrual term is approximated by a finite series of Chebyshev polynomials:

$$\exp(j\Delta\omega(r)t) \approx \sum_{k=0}^{N-1} [c_k(r)T_k(t)] \quad [7]$$

from which conjugate phase reconstruction can be expressed as:

$$m_{CP}(r) = \sum_{k=0}^{N-1} c_k(r) p_k(r) \quad [8]$$

As with the Taylor approximation, in the Chebyshev approximation, N is the number of base images used in the approximation.

Figure 4A:
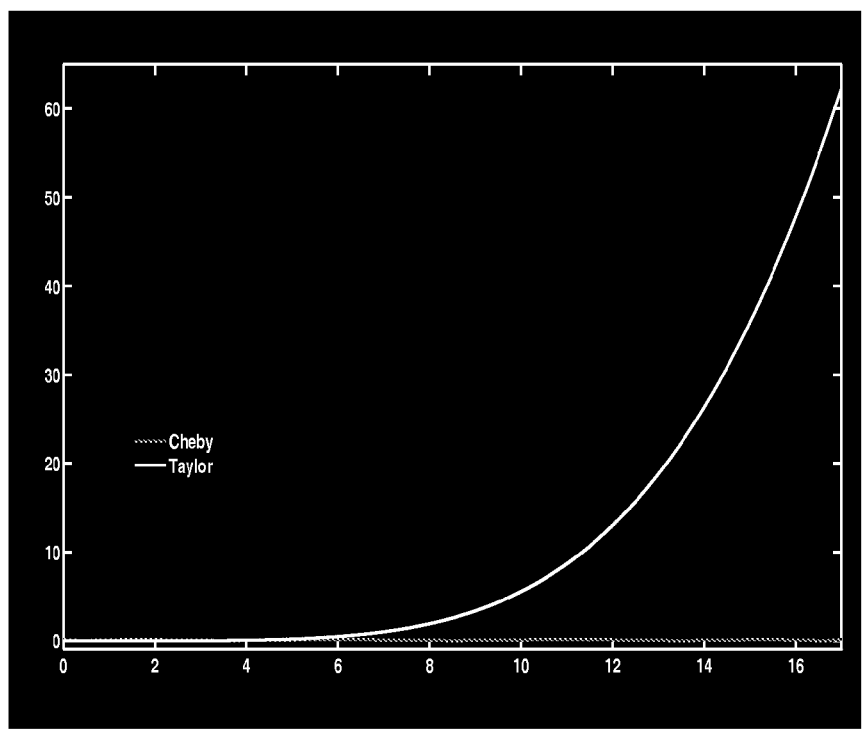
FIGS. 4A and 4B are plots comparing errors for the first and second preferred embodiments.
Figure 4B:
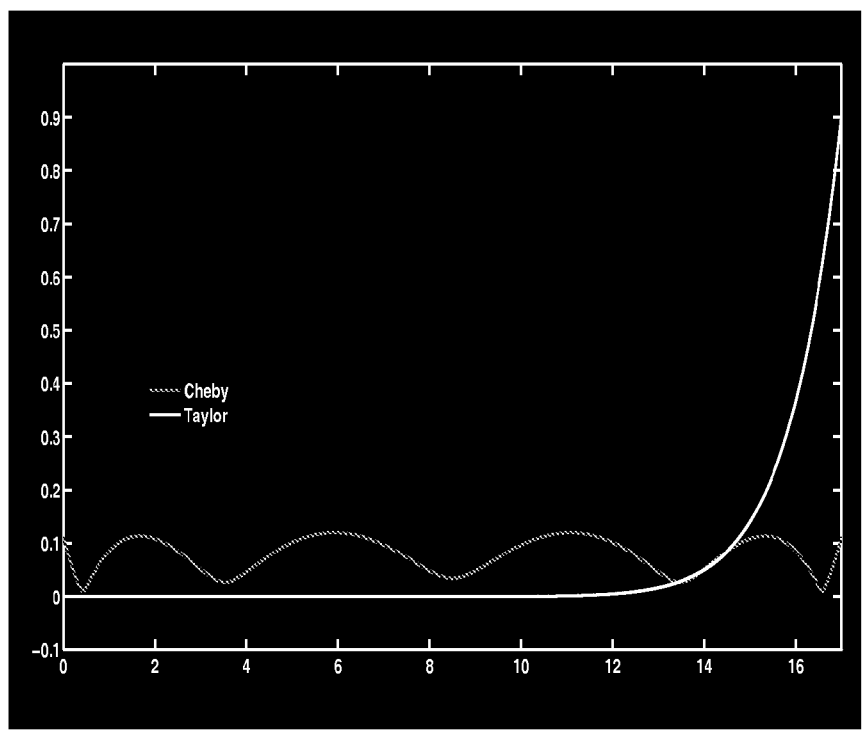

The preferred embodiments will now be compared. FIG. 4A is a plot of the magnitude of the error as a function of time for $\Delta f = 60$ Hz. Both the Taylor and the Chebyshev approximations use five base images. FIG. 4B shows the same thing, except that for the Taylor approximation, 15 base images are used. In both cases, the Chebyshev approximation gives better accuracy.

Figure 5:
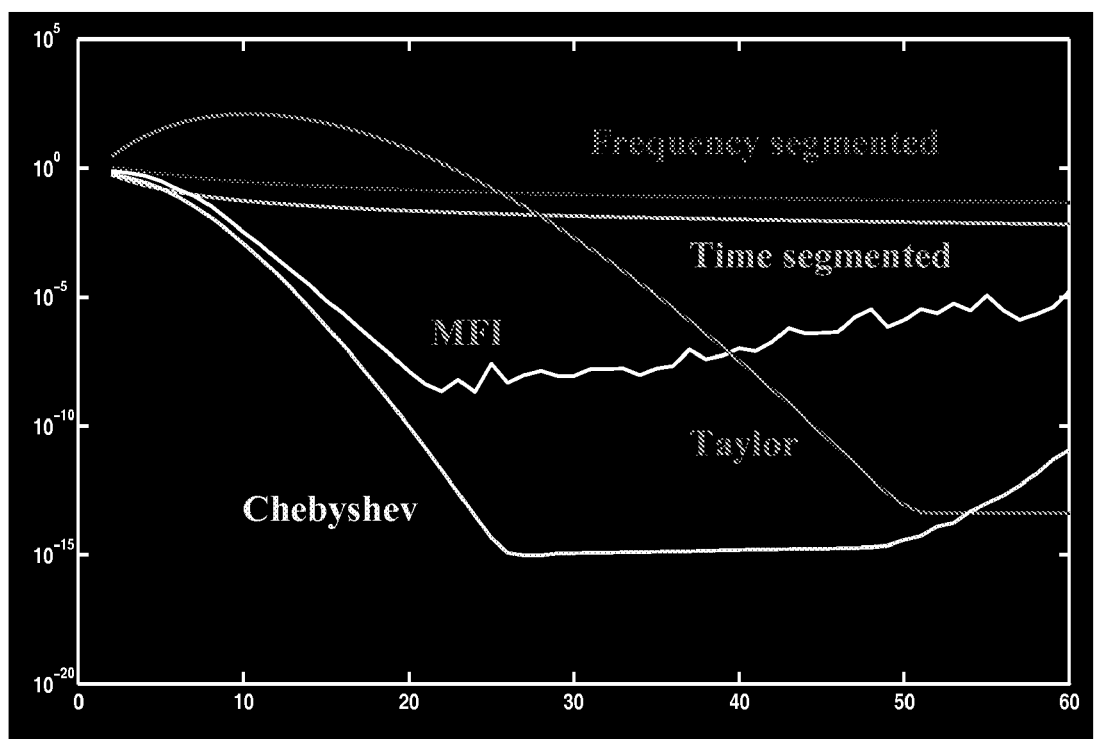
FIG. 5 is a plot of the approximation error to the complex exponential for the first and second preferred embodiments and various other techniques.
Figure 6A:
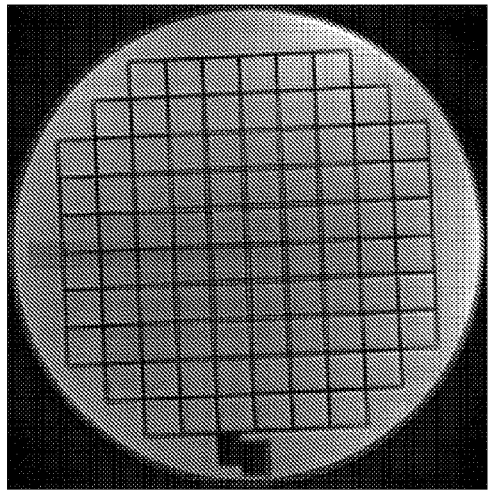
FIGS. 6A-6D are images taken with no correction, conjugate phase correction, the first preferred embodiment, and the second preferred embodiment, respectively.
Figure 6B:
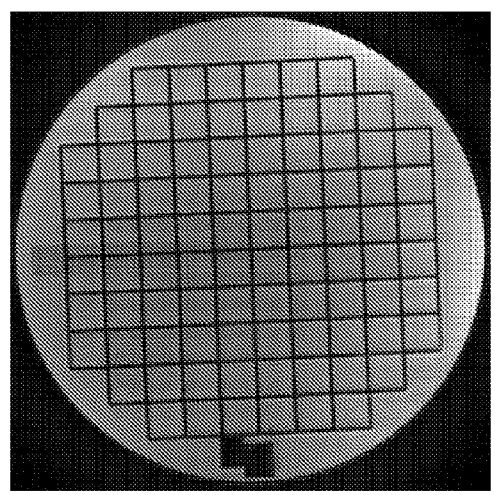
Figure 6C:
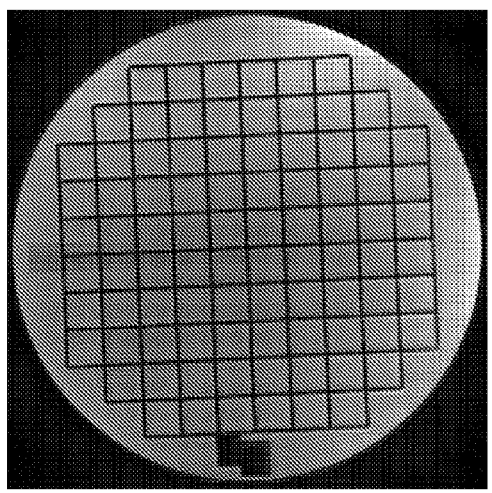
Figure 6D:
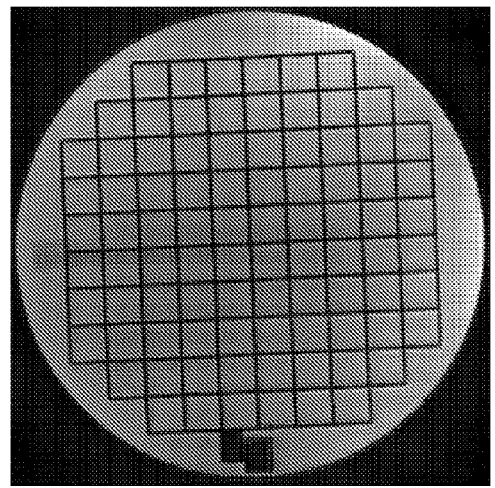

FIG. 5 shows the sum of the magnitude error as a function of the number of base images/segments for the frequency segmented, time segmented, MFI, Taylor, and Chebyshev approximations. The error to $e^{j\Delta\omega(r)t}$ was calculated at each frequency and each time point. The readout was 16.4 ms. The $\Delta f$ range was $[-120\ 120]$ Hz. The readout length was 16.3 ms. A Hanning window was used for time-segmented reconstruction. Depending on the number of base images/segments, either the Taylor or the Chebyshev approximation is the most accurate.

FIGS. 6A-6D show an image of a phantom with no correction, conjugate phase correction, Taylor correction (nine base images), and Chebyshev correction (four base images), respectively. The three types of correction remove the artifacts in the image of FIG. 5A. However, the Taylor and Chebyshev corrections allow greater computational efficiency.

Figure 7:
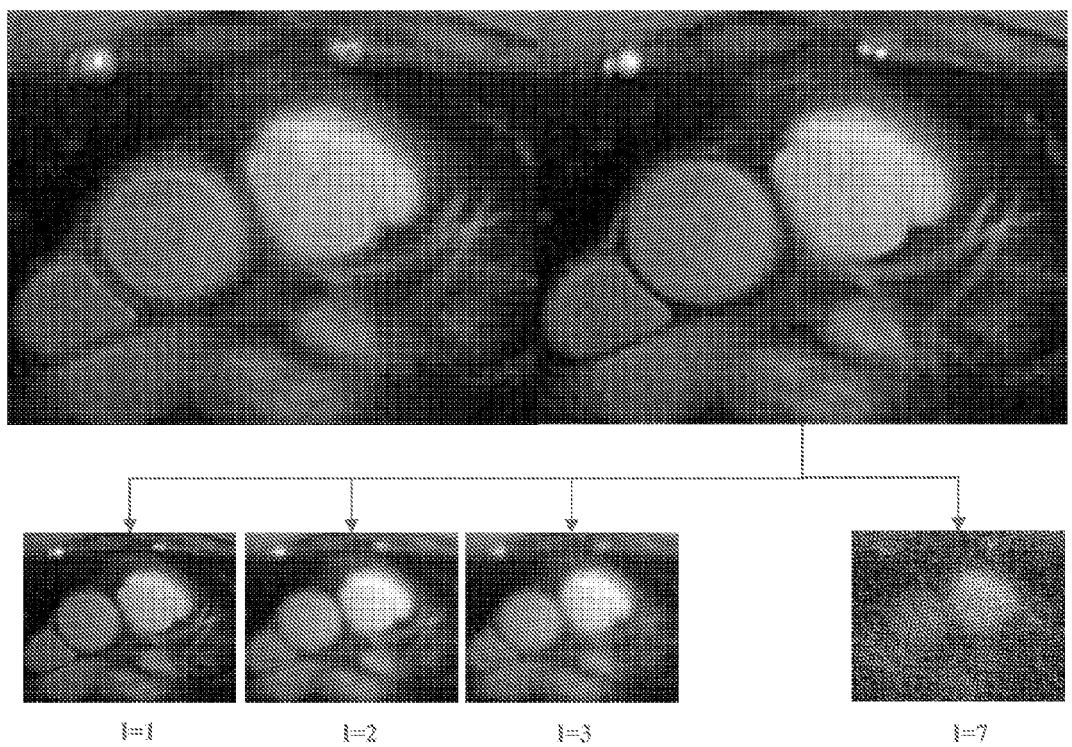
FIG. 7 shows a blurred image and the corresponding deblurred image, along with the corresponding base images that are used to form the deblurred image using a polynomial approximation.

FIG. 7 shows a blurred image and the corresponding deblurred image, along with the corresponding base images that are used to form the deblurred image using a polynomial approximation.

FIGS. 8A-8D show images of a joint with no correction, linear correction, conjugate phase correction, and Chebyshev correction with five base images, respectively. All of the correction techniques remove the artifacts identified by arrows in FIG. 8A. However, the Chebyshev approximation is more computationally accurate than either of the other two.

A variation of the second preferred embodiment uses the Chebyshev approximation to handle the off-resonance effects. Considering the presence of both $B_0$ field inhomogeneity and concomitant gradient fields and ignoring relaxation, the MR signal from an object with spin density m(r) is given by:

$$s(t) = \int m(r) \exp(-i2\pi k(t) \cdot r - i\phi(\Delta\omega(r), \Delta\omega_c(r), t)) dr \quad [9]$$

where k(t) is the k-space trajectory. The off-resonance phase term $\phi(\Delta\omega(r), \Delta\omega_c(r), t)$ can be expressed as:

$$\phi(\Delta\omega(r), \Delta\omega_c(r), t) = \Delta\omega(r) t + \phi_c(\Delta\omega_c(r), t), \quad [10]$$

where $\Delta\omega(r)$ represents the angular off-resonance frequency of $B_0$ field inhomogeneity, and $\phi_c(\Delta\omega_c(r), t)$ represents the off-resonance phase due to concomitant field.

For spiral scanning, King et al (cited above) gave an approximation of the off-resonance phase from the lowest order concomitant field for arbitrary scan plane orientation as follows:

$$\phi_c(\Delta\omega_c(r), t) = \Delta\omega_c(r) t_c, \quad [11]$$

With $$\Delta\omega_c(r) = \gamma \frac{g_m^2}{4B_0}(F_1 X^2 + F_2 Y^2 + F_3 Z^2 + F_4 XZ + F_5 YZ + F_6 XY), \text{ and} \quad [12]$$

$$t_c(t) = \frac{1}{g_m^2} \int_0^t g_0^2(t') dt'. \quad [13]$$

where $B_0$, $g_0(t)$, and $g_m$ are the static field, the amplitude of the readout gradient, and the maximum amplitude of the readout gradient, respectively. $F_1$ to $F_6$ are calculated from the rotation matrix used to rotate from the logical to the physical coordinate system. X and Y are the in-plane coordinates of the logical coordinate system, and Z is the through-plane coordinate of the logical coordinate system. The calculation of $F_1$ to $F_6$ is given in the appendix in King et al.

When the off-resonance varies smoothly in space, CP reconstruction is an effective method of off-resonance correction for various non-Cartesian acquisition methods. CP reconstruction corresponding to Eq. [9] can be expressed as:

$$m(r) = \int s(t) W(t) \exp(i2\pi k(t) \cdot r + i\phi(\Delta\omega(r), \Delta\omega_c(r), t)) dt \quad [14]$$

where W(t) is the density compensation function, which accounts for non-uniform sampling in k-space in non-Cartesian acquisition. W(t) can be calculated from geometric arguments, as the Jacobian of the coordinate transformation or by numerical methods. Noll et al (Noll D C, Fessler J A, Sutton B P. Conjugate phase MRI reconstruction with spatially variant sample density correction *IEEE Trans. Med. Imaging* 2005; 24: 325-336) discussed the implementation of a spatially-varying density compensation function in CP reconstruction.

CP reconstruction is computationally inefficient. Fast alternatives, including time approximation methods, frequency approximation methods, and polynomial approximation methods, have been developed. These methods essentially approximate the off-resonance phase term in different ways to reduce the computational cost of CP reconstruction, and consequently possess different features. Each of these methods was originally developed to correct for B0 field inhomogeneity. Fast CP reconstruction in the presence of both B0 field inhomogeneity and concomitant gradient fields has increased numerical complexity and has not been previously described to our knowledge. Extending the time approximation and frequency approximation methods to produce a combined correction would likely increase computation significantly. As we show below, it is possible to design a particular polynomial approximation that leads to fast and accurate correction for both B0 inhomogeneity and concomitant gradient fields.

Fast conjugate phase reconstruction based on the Chebyshev approximation will now be discussed. Schomberg (Schomberg H, Off-Resonance Correction of MR Images. *IEEE Trans Med Imaging* 1999; 18: 481-495) has previously discussed Chebyshev approximation in CP reconstruction for the purpose of $B_0$ field inhomogeneity correction. In his algorithm, the off-resonance phase term is approximated by a Chebyshev polynomial that is a function of the product of $B_0$ field inhomogeneity and time. One drawback of Schomberg's algorithm is that the calculation of Chebyshev coefficients becomes object dependent, since the field map is involved in the Chebyshev polynomial variable. Another problem associated with Schomberg's algorithm is that it can not be applied for simultaneous B0 field inhomogeneity correction and concomitant gradient field correction.

To address these problems, we propose a fast CP reconstruction algorithm where the off-resonance phase term is approximated by a Chebyshev polynomial in time t. The proposed fast CP reconstruction algorithm can be expressed as follows:

$$m(r) \sum_{k=0}^{N-1} w_k(\Delta\omega(r), \Delta\omega_c(r), \tau) I_k(r) - \frac{1}{2} I_0(r), \quad [15]$$

where $\tau$ is the readout length, $I_k(r)$ are base images, and $w_k(\Delta\omega(r), \Delta\omega_c(r), \tau)$ are constant coefficients whose values depend on the $B_0$ field inhomogeneity, the concomitant gradient field, and the readout length. The mathematical derivation of Eq. [15] is given in Appendix A below. Two forms of Eq. [15], including Eq. [A5] and Eq. [A10], are derived. Our experiments on spiral data sets indicate that these two formulas lead to equivalent off-resonance correction results. The present embodiment can also be easily modified for B0 field inhomogeneity correction or concomitant field correction when only one off-resonance source is present.

The coefficients $w_k(\Delta\omega(r), \Delta\omega_c(r), \tau)$ can be calculated offline and saved as a table at a range of $\Delta\omega(r)$ and $\Delta\omega_c(r)$. The table is object independent and the same table can be used for any data set acquired with same readout length. The table is three dimensional and the length of each dimension corresponds to the number of bins of $\Delta\omega(r)$, the number of bins of $\Delta\omega_c(r)$, and the number of base images, respectively.

Equation [15] involves reconstruction of the time signal s(t) multiplied by $t^l\{l=0,1,2\ldots\}$ followed by a fast reconstruction method such as gridding. To reduce the computational cost, as explained above with reference to FIG. 1, we perform gridding on the time signal s(t) to calculate raw data on a Cartesian grid, and also interpolate the time t onto a Cartesian grid using Delaunay triangulation to form a Cartesian time mask. To compute the base images, we then simply multiply the Cartesian time signal by the time mask multiple times and then perform a Fourier transform. This strategy reduces the number of gridding operations performed during image reconstruction. Since the time mask is only a function of the k-space trajectory, it can also be calculated offline and used for data sets acquired with same k-space trajectory.

The number of base images needed in Eq. [15] is proportional to the range of B0 field inhomogeneity and concomitant gradient field. Center frequency correction can be incorporated into Eq. [15] to reduce the range of B0 field inhomogeneity. When the B0 field map is not highly nonlinear, incorporation of linear off-resonance correction into Eq. [15] is desirable to further reduce the computational cost. To reduce the range of concomitant gradient field, we incorporate linear concomitant gradient correction into Eq. [15]. For a given scan plane orientation, linear concomitant gradient correction reduces the frequency range of an off-center slice to that of a slice at isocenter. The derivation of this is given Appendix B below.

The combination of semi-automatic off-resonance correction and concomitant gradient field correction will now be disclosed. CP reconstruction requires knowledge of accurate off-resonance maps. The off-resonance map from concomitant gradient fields can be calculated from theory. For B0 inhomogeneity correction, a field map is usually acquired by two single shot spirals at different echo times. Such field map acquisitions, however, can be inaccurate in many applications and residual errors can appear in images. Recently, we proposed a method termed semi-automatic off-resonance correction (Chen W, Meyer C H, Semiautomatic off-resonance correction in spiral imaging. *Magn. Reson. Med.* 2008 May; 59(5):1212-9.) to address this problem. In semi-automatic off-resonance correction, the acquired map is used to provide a frequency constraint for following automatic off-resonance correction rather than directly for CP reconstructions.

The computational strategy developed in semi-automatic correction requires calculating the value of individual pixels at an arbitrary constant frequency without reconstructing the whole image at that frequency. Multifrequency interpolation was employed previously for this purpose. Note that the proposed fast CP reconstruction method also has this property. Therefore, the proposed CP reconstruction based on Chebyshev approximation is well suited for combined semi-automatic off-resonance correction and concomitant field correction. To perform combined semi-automatic correction and concomitant field correction, we reconstruct a series of images as follows:

$$m(r;\Delta\omega_i) = \sum_{k=0}^{N-1} w_k(\Delta\tilde{\omega}(r) + \Delta\omega_i, \Delta\omega_c(r), \tau)I_k(r) - \frac{1}{2}I_0(r), \quad [16]$$

$$i = 1, 2 \ldots,$$

where $\Delta\ddot{\omega}(r)$ is the frequency constraint estimated from an acquired low resolution B0 field map and $\Delta\omega_i(i=1, 2\ldots)$ is a series of constant frequency shifts from $\Delta\tilde{\omega}(r)$. Note that concomitant field effects are corrected when reconstructing $m(r;\Delta\omega_i)$ in Eq. [16]. After reconstructing $m(r;\Delta\omega_i)$, semi-automatic correction is then performed for B0 field inhomogeneity correction.

We tested our algorithm on both phantom and in vivo data sets collected by spiral scanning on a Siemens 1.5 T Avanto scanner (Siemens Medical Solutions). We performed the following correction methods and compared the results: (1) concomitant field correction using the proposed method; (2) field-map-based B0 field inhomogeneity correction using fast CP reconstruction; (3) semi-automatic off-resonance correction; (4) combined field-map-based B0 field inhomogeneity correction and concomitant field correction (combined correction A); and (5) combined semi-automatic B0 field inhomogeneity correction and concomitant field correction (combined correction B). For semi-automatic correction and combined correction B, the following parameters are used for the semi-automatic portion of the image reconstruction: the size of summation window was 15×15; the power α of the objective function was 1; the searching range of the off-resonance frequency shift was from −50 Hz to 50 Hz; the increment of searching frequencies was 10 Hz; and the first 1.6 ms of the readout was used to reconstruct the low resolution images (after concomitant gradient field correction) whose phase was then removed from corresponding high resolution images before objective function calculation. The value of each of these parameters was the same as those specified in our above-cited 2008 paper. To account for trajectory errors due to gradient delay and eddy current effects, modified k-space trajectories based on methods described by Tan et al (Tan H, Meyer C H, K-space trajectory estimation in spiral imaging. Proc., ISMRM, 15th Annual Meeting, Berlin, 2007, 981) were used for image reconstruction.

A 3-D table of interpolation coefficients was precalculated for the present embodiment and used for each of the data sets acquired with the same readout length. The 3-D table was calculated with B0 field inhomogeneity from −100 Hz to 100 Hz with a 1 Hz frequency increment, concomitant field off-resonance frequency $$\left(=\frac{\Delta\omega_c}{2\pi}\right)$$

from −100 Hz to 100 Hz with a 1 Hz increment, and 12 base images. The specified range of concomitant field is sufficient in our application after incorporating linear concomitant field correction. For combined semi-automatic off-resonance correction and concomitant correction, an additional 3D table was precalculated with the same range of B0 field inhomogeneity and concomitant field but with only 5 base images due to significantly reduced readout length.

Figure 9A:
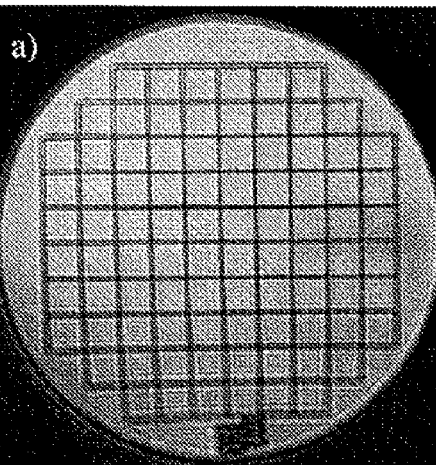
FIGS. 9A-9F show images of a resolution phantom with different off-resonance correction methods.
Figure 9B:
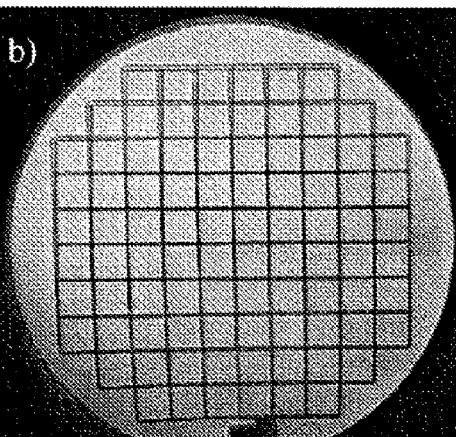
Figure 9C:
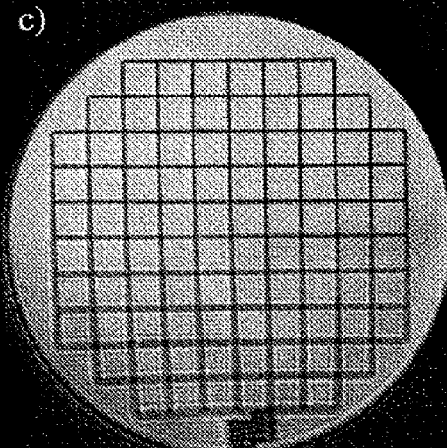
Figure 9D:
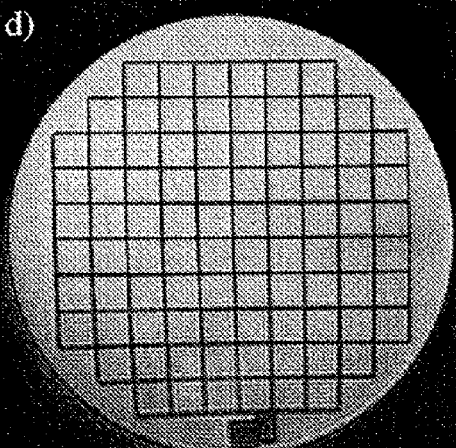
Figure 9E:
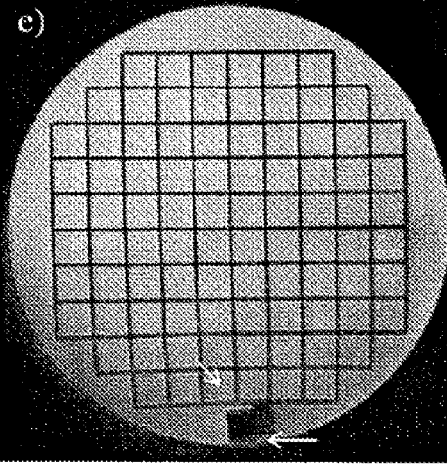
Figure 9F:
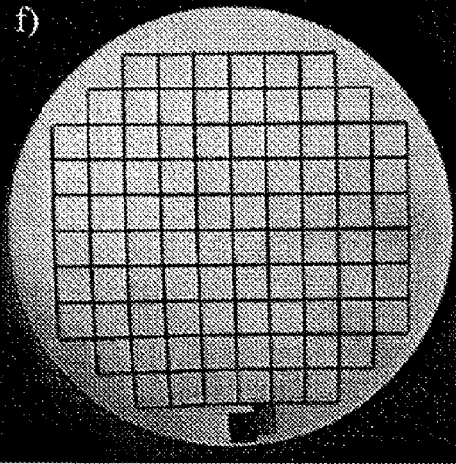

We performed combined correction based on Eq. [A5] and Eq. [A10] on the data sets we acquired and found the results were equivalent. FIGS. 9A-9F show the results for a coronal scan of a resolution phantom. The parameters of the spiral sequence are as follows: 14 interleaves with 8192 samples and 2 microseconds ADC dwell time per interleaf, 5 mm slice thickness, and 512 by 512 reconstructed image matrix. A low resolution field map was acquired using two single shot spirals with 1 ms echo delay. The imaging slice was 6.4 cm off isocenter along the transverse direction, 2.3 cm off isocenter along the sagittal direction, and 1.4 cm off isocenter along the coronal direction. FIG. 9A is the image with no off-resonance correction. FIG. 9B is the result after concomitant gradient correction. Note that there is significant deblurring of concomitant field effects at the bottom of the image, but that the B0 blurring is still obvious at the top of the image. FIG. 9C is the result after B0 inhomogeneity correction using fast CP reconstruction. Note that now the B0 blurring artifacts are removed but the concomitant field blurring is obvious. FIG. 9D is the result after semi-automatic off-resonance correction. Note that semi-automatic correction can provide both B0 inhomogeneity correction and moderate concomitant field correction, but residual concomitant field blurring is still obvious. FIGS. 9E and 9F are combined correction A and B, respectively. Both combined correction methods achieved simultaneous B0 inhomogeneity correction and concomitant field correction. Compared to FIG. 9E, FIG. 9F shows better deblurring in regions indicated by the white arrows in FIG. 9E, indicating the inaccuracy of the acquired B0 field map in these regions.

Figure 10A:
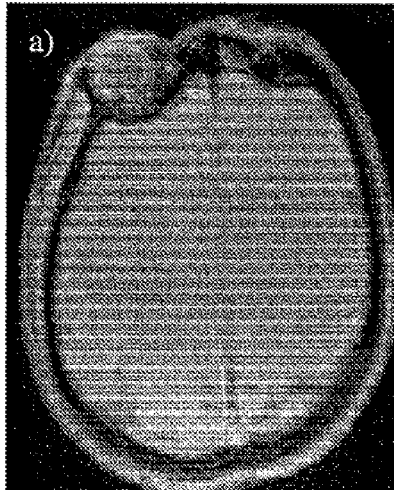
FIGS. 10A-10F show head images of a normal volunteer with different off-resonance correction methods.
Figure 10B:
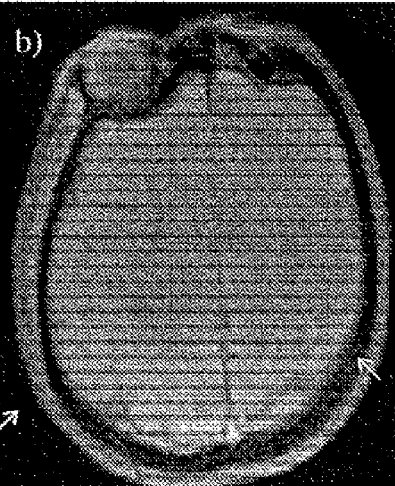
Figure 10C:
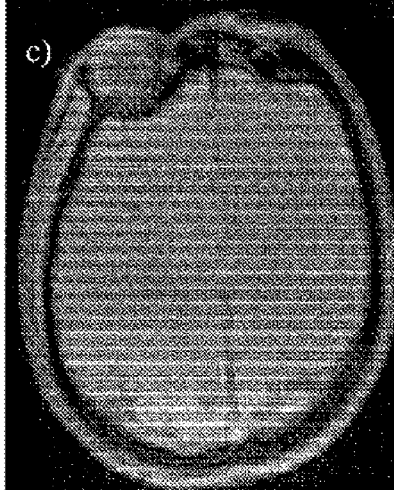
Figure 10D:
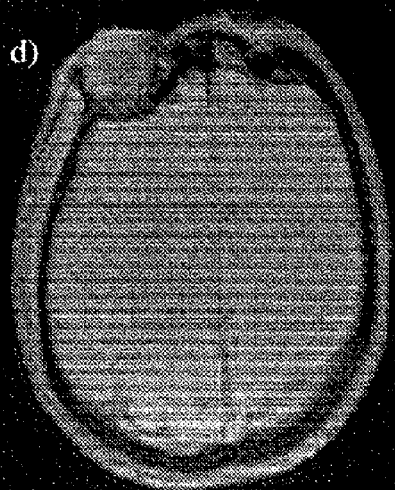
Figure 10E:
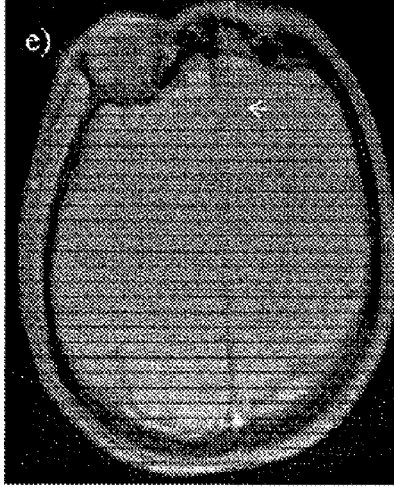
Figure 10F:
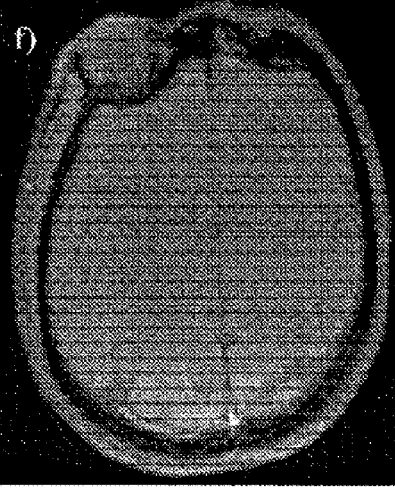

FIGS. 10A-10F are an example of an in vivo double-oblique head scan of a normal volunteer. The imaging slice was 8.4 cm off isocenter along the transverse direction, 2.6 cm off isocenter along the sagittal direction, and 4.8 cm off isocenter along the coronal direction. The imaging plane was tilted 30 degrees from transverse to coronal and then tilted 15 degrees from coronal toward sagittal. We used the method described by Wang et al (Wang W-T, Hu P, Meyer C H. Estimating spatial resolution of in vivo magnetic resonance images using radiofrequency tagging pulses. *Magn Reson Med.* 2007 July; 58:190-199.) to create tagging lines to make off-resonance blurring more prominent. Twenty spiral interleaves with 8192 samples per interleaf and 2 microseconds ADC dwell time were used to acquire the data set. Other sequence parameters are the same as those used to acquire the data set in FIGS. 9A-9F. FIG. 10A is the image without any off-resonance correction. FIG. 10B is the image after concomitant field correction using the proposed method. The deblurring is significant after concomitant correction, since the concomitant gradient field is severe in this scan plane. However, the residual blurring is still obvious in regions indicated by the white arrows due to the local B0 field inhomogeneity effects. FIG. 10C is the image after B0 inhomogeneity correction using fast CP reconstruction and FIG. 10D is the image after semi-automatic correction. The blurring artifacts are significant in both images due to the strong off-resonance effects from concomitant gradient field. FIG. 10E and FIG. 10F are the combined correction A and B, respectively. Both images are sharper than FIG. 10B. The tagging lines in FIG. 10F is better defined than those in FIG. 10E in the region indicated by the white arrow in FIG. 10E, indicating the inaccuracy of acquired the low-resolution B0 field map at this region.

Appendix A:

The approximation to off-resonance phase by Chebyshev polynomial in t can be expressed as (29):

$$\phi(\Delta\omega(r), \Delta\omega_c(r), t) = \sum_{k=0}^{N-1} [c_k(\Delta\omega(r), \Delta\omega_c(r), \tau)T_k(t)] - \frac{1}{2}c_0 \quad [A1]$$

where $\tau$ is readout length and $T_k(t)$ are Chebyshev polynomials defined as $T_0 = 1;$ $$T_1(t) = \left(\frac{2t}{\tau} - 1\right),$$

and $$T_{n+1}(t) = 2\left(\frac{2t}{\tau} - 1\right)T_n(t) - T_{n-1}(t), n \geq 1, \quad [A2]$$

and $c_k(\Delta\omega(r),\Delta\omega_c(r),\tau)$ are coefficients that depend on the strength of B0 field inhomogeneity $\Delta\omega(r)$, the strength $\Delta\omega_c(r)$, and readout length $\tau$. $c_k(\Delta\omega(r),\Delta\omega_c(r),\tau)$ can be calculated as follows (29):

$$c_k(\Delta\omega(r), \Delta\omega_c(r), \tau) = \quad [A3]$$

$$\frac{2}{N}\sum_{n=1}^{N}\left[\cos\left(\frac{\pi(k-0.5)}{N}\right)\phi\left(\Delta\omega(r), \Delta\omega_c(r), \frac{\tau}{2}\left(\cos\left(\frac{\pi(n-0.5)}{N}\right)+1\right)\right)\right]$$

Note the Chebyshev polynomial $T_k(t)$ in Eq. [A2] can be expressed in polynomial form:

$$T_k(t) = \sum_{l=0}^{k} b_l^{(k)}\left(\frac{2t}{\tau} - 1\right)^l, \quad [A4]$$

where $b_l^{(k)}$ is the $l^{th}$ coefficient term for $T_k(t)$. Combining Eq. [A1], Eq. [A4] and Eq. [6], after mathematical rearrangement, we have:

$$m(r) = \sum_{k=0}^{N-1} c_k(\Delta\omega(r), \Delta\omega_c(r), \tau)p_k(r) - \frac{1}{2}p_0(r) \quad [A5]$$

where $$p_k(r) = \sum_{l=0}^{k} b_l^{(k)} q_l(r), \quad [A6]$$

with $$q_l(r) = \int_t s(t)\left(\frac{2t}{\tau} - 1\right)^l W(t)\exp(j(2\pi k(t)\cdot r)dt \quad [A7]$$

Here $q_l(r)$ denotes a series of images which can be reconstructed by replacing the signal s(t) with $$s(t)\left(\frac{2t}{\tau} - 1\right)^l$$

followed by gridding reconstruction or other fast reconstruction methods. Possibilities include exchanging the sequence of gridding and multiplication to reduce the number of gridding operations.

Eq. [A5], [A6], and [A7] represent a direct implementation of Chebyshev approximation for fast CP reconstruction. A more computationally efficient implementation for fast CP reconstruction is to use the polynomial form of Chebyshev approximation. Note that by combining Eq. [A1] and Eq. [A4] and after mathematical simplification, we have:

$$\phi(\Delta\omega(r), \Delta\omega_c(r), t) = \sum_{k=0}^{N-1}\left[h_k(\Delta\omega(r), \Delta\omega_c(r), \tau)\left(\frac{2t}{\tau} - 1\right)^k\right] - \frac{1}{2}c_0 \quad [A8]$$

where $$h_k(\Delta\omega(r), \Delta\omega_c(r), \tau) = \sum_{k=0}^{N-1}\left[\sum_{i=k}^{N-1}[b_k^{(i)}c_i(\Delta\omega(r), \Delta\omega_c(r), \tau)]\right] \quad [A9]$$

Substituting Eq. [A7] into Eq. [6], we have:

$$m(r) = \sum_{k=0}^{N-1} h_k(\Delta\omega(r), \Delta\omega_c(r), \tau)q_k(r) - \frac{1}{2}q_o(r) \quad [A10]$$

where $q_k(r)$ are same images as defined in Eq. [A7].

Eq. [A10] is another approach for fast CP reconstruction based on Chebyshev approximation. Compared to Eq. [A5], Eq. [A10] is more computationally efficient, since Eq. [A5] involves an additional combination of images. We found both methods achieved equivalent results on the spiral data sets we acquired.

Appendix B:

The concomitant gradient field, as given in [4] is:

$$\Delta\omega_c(r) = \gamma\frac{g_0^2(t')}{4B_0}(F_1 X^2 + F_2 Y^2 + F_3 Z^2 + F_4 XZ + F_5 YZ + F_6 XY) \quad [B1]$$

Assuming a fixed scan plan orientation, $F_1$ through $F_6$ and Z are constant throughout the rest of this derivation. Adding an offset of A, B, C to the scan plane in the X, Y, and Z axes leads to [B2]:

$$\Delta\omega_c(r) = \gamma\frac{g_0^2(t')}{4B_0}\begin{pmatrix} F_1(X+A)^2 + F_2(Y+B)^2 + F_3(Z+C)^2 + \\ F_4(X+A)(Z+C) + F_5(Y+B)(Z+C) + \\ F_6(X+A)(Y+B) \end{pmatrix} \quad [B2]$$

Expansion of the squared terms in [B2] leads to [B3]

$$\Delta\omega_c(r) = \quad [B3]$$

$$\gamma\frac{g_0^2(t')}{4B_0}\begin{pmatrix} F_1(X^2 + 2XA + A^2) + F_2(Y^2 + 2YB + B^2) + \\ F_3(Z^2 + 2ZC + C^2) + F_4(XZ + XC + AZ + AC) + \\ F_5(YZ + YC + BZ + BC) + F_6(XY + XB + AY + AB) \end{pmatrix}$$

Collecting all the terms in [B3] into 3 categories (constant, linear, and squared) leads to [B4]

$$\Delta\omega_c(r) = \quad [B4]$$

$$\gamma\frac{g_0^2(t')}{4B_0}\begin{pmatrix} [F_1 X^2 + F_2 Y^2 + F_3 Z^2 + F_4 XZ + F_5 YZ + F_6 XY] + \\ [F_1 2XA + F_2 2YB + F_4 XC + F_5 YC + F_6 XB + F_6 AY] + \\ [F_1 A^2 + F_2 B^2 + F_3 C^2 + F_3 2ZC + F_4 AC + F_4 AZ + \\ F_5 BC + F_5 BZ + F_6] \end{pmatrix}$$

Concomitant linear correction applies a linear fit to the concomitant field, with a spatially constant $f_0$ term and gradients in the X and Y directions. The constant term is used to demodulate the raw data, and the gradients to warp the k-space trajectory. Mathematically:

$$\Delta\ddot{\omega}_c(r) = f_0 + \alpha X + \beta Y \quad [B5]$$

$$s'(t) = s(t)\exp[2\pi f_0 t_c]$$

$$k'_x(t) = k_x(t)\alpha t,$$

$$k'_x(t) = k_x(t)\alpha t_c \quad [B6]$$

The linear fit will completely remove off-resonance phase due to the $2^{nd}$ and $3^{rd}$ square brackets in [B4], as those terms are either constant or linear in X or Y. The remaining terms in [B4], given in [B7], are identical to [B1]. These terms in [B7], which are all square and cross terms, will be partially corrected by the linear fit, principally by the center frequency term.

$$\Delta\omega_c(r) = \gamma\frac{g_0^2(t')}{4B_0}(F_1 X^2 + F_2 Y^2 + F_3 Z^2 + F_4 XZ + F_5 YZ + F_6 XY) \quad [B7]$$

For a fixed scan plane orientation, the linear concomitant correction completely removes any blurring due to phase resulting from off-center terms (the $2^{nd}$ and $3^{rd}$ square brackets in [B4]). The residual blurring pattern is the same as that of an isocenter scan that has been linear corrected.

Figure 11:
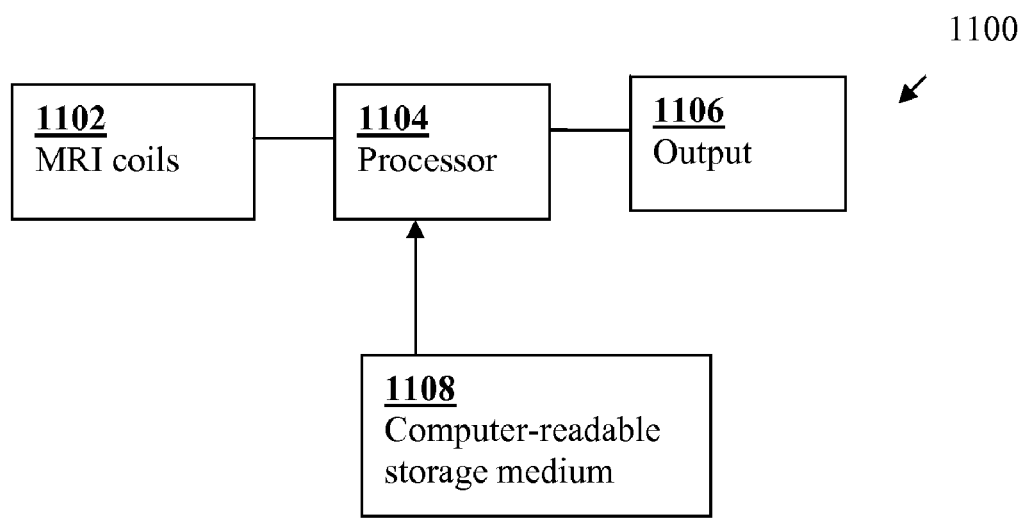
FIG. 11 is a schematic diagram of a system on which the present invention can be implemented.

FIG. 11 is a schematic diagram of a system 1100 on which any of the preferred embodiments, or any other embodiment, can be implemented. The system includes MR coils 1102 for taking raw image data from the subject, a processor 1104 for performing any of the operations described above, and an output 1106 for outputting the image. The output 1106 can include one or more of a display, a printer, and a transmission line for transmitting the image to a remote location. Code for performing the above operations can be supplied to the processor on any suitable computer-readable medium 1108.

While preferred embodiments of the invention have been set forth above, those skilled in the art who have reviewed the present disclosure will readily appreciate that other embodiments can be realized within the scope of the invention. For example, numerical values are illustrative rather than limiting. Therefore, the present invention should be construed as limited only by the appended claims.

We claim:

1. A method for reconstructing an image of an object, the method comprising:
   (a) taking a time signal of raw image data of the object;
   (b) approximating a conjugate phase reconstruction of the image by approximating an off-resonance phase accrual term by a finite polynomial expansion; and
   (c) reconstructing the image in accordance with the raw image data taken in step (a) and the conjugate phase reconstruction approximated in step (b).

2. The method of claim 1, wherein the raw image data comprise magnetic resonance image data.

3. The method of claim 1, wherein the finite polynomial expansion is a finite Taylor expansion.

4. The method of claim 1, wherein the finite polynomial expansion is a finite Chebyshev expansion.

5. The method of claim 1, wherein each term in the finite polynomial expansion has, as a factor, one of a plurality of base images of the object.

6. The method of claim 5, wherein the base images are reconstructed from the raw image data by gridding.

7. The method of claim 6, wherein the gridding is performed by:
   (i) gridding the time signal to acquire a Cartesian time signal;
   (ii) interpolating time onto a Cartesian grid to form a Cartesian time mask; and
   (iii) computing the base images from the Cartesian time signal and the Cartesian time mask.

8. The method of claim 7, wherein the time is interpolated onto the Cartesian grid using Delaunay triangulation.

9. The method of claim 1, wherein step (b) comprises correcting for both main field inhomogeneity and concomitant gradient effects.

10. A system for reconstructing an image of an object, the system comprising:
   an imaging apparatus for taking a time signal of raw image data of the object;
   a processor, in communication with the imaging apparatus, configure to approximate a conjugate phase reconstruction of the image by approximating an off-resonance phase accrual term by a finite polynomial expansion and reconstructing the image in accordance with the raw image data and the approximated conjugate phase reconstruction; and
   an output, in communication with the processor, for outputting the reconstructed image.

11. The system of claim 10, wherein the imaging apparatus is a magnetic resonance imaging apparatus, and wherein the raw image data comprise magnetic resonance image data.

12. The system of claim 10, wherein the finite polynomial expansion is a finite Taylor expansion.

13. The system of claim 10, wherein the finite polynomial expansion is a finite Chebyshev expansion.

14. The system of claim 10, wherein each term in the finite polynomial expansion has, as a factor, one of a plurality of base images of the object.

15. The system of claim 14, wherein the base images are reconstructed from the raw image data by gridding.

16. The system of claim 15, wherein the gridding is performed by:
   (i) gridding the time signal to acquire a Cartesian time signal;
   (ii) interpolating time onto a Cartesian grid to form a Cartesian time mask; and
   (iii) computing the base images from the Cartesian time signal and the Cartesian time mask.

17. The system of claim 16, wherein the time is interpolated onto the Cartesian grid using Delaunay triangulation.

18. The system of claim 10, wherein the processor corrects for both main field inhomogeneity and concomitant gradient effects.

19. A non-transitory computer-readable storage medium encoded with a computer program for reconstructing an image of an object which when implemented on a processor in an imaging system causes the processor to perform the steps of:
   (a) taking a time signal of raw image data of the object;
   (b) approximating a conjugate phase reconstruction of the image by approximating an off-resonance phase accrual term by a finite polynomial expansion; and
   (c) reconstructing the image in accordance with the raw image data taken in step (a) and the conjugate phase reconstruction approximated in step (b).

20. The non-transitory computer-readable storage medium of claim 19, wherein the raw image data comprise magnetic resonance image data.

21. The non-transitory computer-readable storage medium of manufacture of claim 19, wherein the finite polynomial expansion is a finite Taylor expansion.

22. The non-transitory computer-readable storage medium of claim 19, wherein the finite polynomial expansion is a finite Chebyshev expansion.

23. The non-transitory computer-readable storage medium of claim 19, wherein each term in the finite polynomial expansion has, as a factor, one of a plurality of base images of the object.

24. The non-transitory computer-readable storage medium of claim 23, wherein the base images are reconstructed from the raw image data by gridding.

25. The non-transitory computer-readable storage medium of claim 24, wherein the gridding is performed by:
   (i) gridding the time signal to acquire a Cartesian time signal;
   (ii) interpolating time onto a Cartesian grid to form a Cartesian time mask; and
   (iii) computing the base images from the Cartesian time signal and the Cartesian time mask.

26. The non-transitory computer-readable storage medium of claim 24, wherein the time is interpolated onto the Cartesian grid using Delaunay triangulation.

27. The non-transitory computer-readable storage medium of claim 19, wherein step (b) comprises correcting for both main field inhomogeneity and concomitant gradient effects.

28. A method for reconstructing an image of an object, the method comprising:
   (a) taking a time signal of raw image data of the object;
   (b) correcting the raw image data for both main field inhomogeneity and concomitant gradient effects; and
   (c) reconstructing the image in accordance with the raw image data as corrected in step (b).

* * * * *

UNITED STATES PATENT AND TRADEMARK OFFICE
CERTIFICATE OF CORRECTION

PATENT NO. : 8,094,907 B1
APPLICATION NO. : 12/114307
DATED : January 10, 2012
INVENTOR(S) : Craig H. Meyer et al.

Page 1 of 1

It is certified that error appears in the above-identified patent and that said Letters Patent is hereby corrected as shown below:

Title Page, Item (73) Assignee: University of Virginia should read --  Assignee: University of Virginia Patent Foundation

Signed and Sealed this
Twenty-sixth Day of June, 2012

David J. Kappos
*Director of the United States Patent and Trademark Office*